United States Patent [19]
Chen et al.

[11] Patent Number: 6,033,555
[45] Date of Patent: Mar. 7, 2000

[54] SEQUENTIAL CATALYTIC AND THERMAL CRACKING FOR ENHANCED ETHYLENE YIELD

[75] Inventors: Tan-Jen Chen; Luc Roger Marc Martens, both of Kingwood, Tex.

[73] Assignee: Exxon Chemical Patents Inc., Houston, Tex.

[21] Appl. No.: 08/872,660

[22] Filed: Jun. 10, 1997

[51] Int. Cl.$^7$ .................................................. C10G 51/02
[52] U.S. Cl. ........................ 208/52 R; 208/72; 208/73; 208/77; 208/113
[58] Field of Search ................... 208/521 R, 72, 208/73, 77, 113

[56] References Cited

U.S. PATENT DOCUMENTS

| | | | |
|---|---|---|---|
| Re. 28,341 | 2/1975 | Wadlinger et al. | 208/120 |
| Re. 29,949 | 4/1979 | Churchill | 29/611 |
| 2,882,243 | 4/1959 | Milton | 252/455 |
| 2,882,244 | 4/1959 | Milton | 252/455 |
| 2,940,840 | 6/1960 | Shapleigh | 48/215 |
| 3,130,007 | 4/1964 | Breck | 23/113 |
| 3,216,789 | 11/1965 | Breck | 23/113 |
| 3,247,195 | 4/1966 | Kerr | 260/242 |
| 3,308,069 | 3/1967 | Wadlinger et al. | 252/455 |
| 3,360,587 | 12/1967 | Adams | 260/683 |
| 3,702,292 | 11/1972 | Burich | 208/80 |
| 3,702,886 | 11/1972 | Argaurer | 423/328 |
| 3,709,979 | 1/1973 | Chu | 423/328 |
| 3,766,278 | 10/1973 | Bogart et al. | 260/683 |
| 3,832,449 | 8/1974 | Rosinski et al. | 423/329 |
| 3,862,898 | 1/1975 | Boyd et al. | 208/73 |
| 3,882,243 | 5/1975 | Maeda et al. | 424/312 |
| 4,016,245 | 4/1977 | Plank et al. | 423/448 |
| 4,046,859 | 9/1977 | Plank et al. | 423/328 |
| 4,076,842 | 2/1978 | Rosinski et al. | 423/328 |
| 4,137,147 | 1/1979 | Franck et al. | 208/61 |
| 4,229,424 | 10/1980 | Kokotailo | 423/328 |
| 4,238,318 | 12/1980 | Kouwenhoven et al. | 208/120 |
| 4,282,085 | 8/1981 | O'Rear et al. | 208/120 |
| 4,388,175 | 6/1983 | Lionetti et al. | 208/74 |
| 4,397,827 | 8/1983 | Chu | 423/326 |
| 4,487,985 | 12/1984 | Tabak | 585/517 |
| 4,556,447 | 12/1985 | Bradley et al. | 156/578 |
| 4,560,536 | 12/1985 | Tabak | 422/116 |
| 4,584,091 | 4/1986 | Pine | |
| 4,954,325 | 9/1990 | Rubin et al. | 423/328 |
| 5,264,115 | 11/1993 | Mauleon et al. | 208/67 |
| 5,348,924 | 9/1994 | Potter et al. | 502/66 |
| 5,506,365 | 4/1996 | Mauleon et al. | 585/329 |
| 5,523,502 | 6/1996 | Rubin | 585/324 |
| 5,552,035 | 9/1996 | Potter et al. | 208/135 |

FOREIGN PATENT DOCUMENTS

| | | |
|---|---|---|
| 0 023 802 | 2/1981 | European Pat. Off. . |
| 0 127 399 | 12/1984 | European Pat. Off. . |
| 0 262 049 | 3/1988 | European Pat. Off. . |
| 395345 | 10/1990 | European Pat. Off. . |
| 60-235890 | 11/1985 | Japan . |
| 63-010693 | 1/1988 | Japan . |
| 2 105 362 | 3/1983 | United Kingdom . |
| WO 86/02376 | 4/1986 | WIPO . |
| WO 95/13255 | 5/1995 | WIPO . |

OTHER PUBLICATIONS

"Atlas of Zeolite Structure Types" by W. M. Meier, D. H. Olson and C. Baerlocher (4th ed., Butterworths/Intl. Zeolite Assoc. [1996]).

*Primary Examiner*—Helane Myers

[57] ABSTRACT

The invention provides a process for improving the conversion of a hydrocarbon feedstock to light olefins comprising the steps of first contacting the hydrocarbon feedstock with a light olefin producing cracking catalyst and subsequently thermally cracking the unseparated stream to produce additional ethylene. Preferably the zeolite catalyst is selected from the group consisting of ferrierite, heulandite, phillipsite, faujasite, chabazite, erionite, mordenite, offretite, gmelinite, analcite, ZSM-5, ZSM-11, ZSM-25, gallium silicate zeolite, zeolite Beta, zeolite rho, ZK5, titanosilicate, zeolites having a silica to alumina molar ratio within the range of about 2.0:1 to 2000:1 ferrosilicate; zeolites such as those described in U.S. Pat. No. 4,238,318; borosilicate zeolites such as those described in Belgian Pat. No. 859656; zeolites designated by the Linde Division of Union Carbide by the letters of X, Y, A, L; zeolites such as those described in U.S. Pat. No. 5,552,035; and zeolites such as those described in U.S. Pat. No. 5,348,924. Preferably the catalyst is contacted at a temperature within the range of about 500° C. to about 750° C. and the feedstock flows at a weight hourly space velocity in the range of about 0.1 Hr$^{-1}$ WHSV to about 100 Hr$^{-1}$WHSV. The trim thermal cracking is carried out between 650° C. to 900° C. for 0.1 to 20 seconds.

20 Claims, No Drawings

SEQUENTIAL CATALYTIC AND THERMAL CRACKING FOR ENHANCED ETHYLENE YIELD

FIELD OF THE INVENTION

The invention provides a process for increasing yield of ethylene in a catalytic cracking process by use of a thermal cracking step after catalytic cracking.

BACKGROUND OF THE INVENTION

Thermal and catalytic conversion of hydrocarbons to olefins is an important industrial process producing billions of pounds of olefins each year. Because of the large volume of production, small improvements in operating efficiency translate into significant profits. Catalysts play an important role in more selective conversion of hydrocarbons to olefins.

Particularly important catalysts are found among the natural and synthetic zeolites. Zeolites are complex crystalline aluminosilicates which form a network of $AlO_4$ and $SiO_4$ tetrahedra linked by shared oxygen atoms. The negative charge of the tetrahedra is balanced by the inclusion of protons or cations such as alkali or alkaline earth metal ions. The interstitial spaces or channels formed by the crystalline network enable zeolites to be used as molecular sieves in separation processes. The ability of zeolites to adsorb materials also enables them to be used in catalysis. There are a large number of both natural and synthetic zeolitic structures. The wide breadth of such numbers may be understood by considering the work "Atlas of Zeolite Structure Types" by W. M. Meier, D. H. Olson and C. Baerlocher (4th ed., Butterworths/Intl. Zeolite Assoc. [1996]). Catalysts containing zeolites have been found to be active in cracking light naphtha to ethylene and propylene, the prime olefins.

Of particular interest are the acidified zeolites effective for conversion of light hydrocarbons such as low boiling naphthas to the prime olefins. Typical catalysts include ZSM-5 zeolite described and claimed in U.S. Pat. No. 3,702,886, and ZSM-11 described in U.S. Pat. No. 3,709,979, and the numerous variations on these catalysts disclosed and claimed in later patents.

Previous uses of multiple reaction or temperature zones in prime olefin production have used hydrocracking or hydrogenolysis to produce ethane and propane with little production of prime olefins in the first stages. Franck et al., U.S. Pat. No. 4,137,147 used multiple hydrogenolysis stages to which each stage operated at 5° C. to 25° C. higher than the preceding stage. The light hydrocarbons up to $C_3$ in the effluent from the hydrogenolysis stages were then steam cracked to prime olefins, while the $C_4+$ production was separated and at least part of it sent to further hydrogenolysis for additional ethane and propane production. The steam cracking unit was supplied a fraction consisting essentially of ethane and propane for conversion to ethylene. Lionetti et al., U.S. Pat. No. 4,388,175, discloses a two stage system for production of aromatics from heavy oil. The second stage is operated at a higher temperature than the first to produce light naphtha, gasoline and needle coke. There was no indication of any application to prime olefins production. Tabak, U.S. Pat. No. 4,487,985 and its divisional U.S. Pat. No. 4,560,536 teaches oligomerization of lower olefins in a multistage series of reactors wherein catalyst partially inactivated in the primary stage is employed at a higher temperature in a secondary stage prior to catalyst regeneration. In European patent application 0 023 802 a hydrocracking step produces $C_2$ to $C_5$ alkanes from which prime olefins are produced by downstream thermal cracking at a higher temperature. GB 2,105,362 teaches a two stage thermal cracking process in a catalyst free system wherein the first reaction zone heats the steam/feedstock from 800° C. to 1000° C. and then passes the feedstock to a second catalyst free zone where it is heated from 850° C. to 1150° C. Mauleon et al., U.S. Pat. Nos. 5,506,365 and 5,264,115, teach a multiple zone process wherein hot catalyst is used in a mild steam thermal cracking process and reacted further downstream with additional catalyst at a lower temperature in a process aimed at gasoline production.

European Patent Application 0 262 049 teaches steam cracking of hydrocarbons (propane is exemplified) followed by contact with a multi-component zeolite-containing catalyst. The thermal cracking unit is operated at a higher temperature than the downstream catalytic cracker. Adams, U.S. Pat. No. 3,360,587, also teaches a steam cracking step followed by a catalytic cracker, again the catalytic cracker is at a lower temperature than the upstream thermal cracker. In European patent application 0 023 802 a catalytic (hydrocracking) reaction stage produces mainly $C_2$ to $C_5$ paraffins which are subsequently fed to an optional higher temperature thermal cracking unit for conversion to prime olefins. Published PCT application WO 95/13255 describes an integrated system wherein a light fraction is separated from the effluent of a deep catalytic cracking unit running on a relatively heavy oil fraction and recycled to a thermal cracking unit to produce prime olefins. Published PCT application WO 86/02376 discloses heavy oil cracking including a pre-pyrolysis cracking step followed by separation of an overhead stream that is thermally cracked for prime olefin production. Burich, U.S. Pat. No. 3,702,292, discloses an integrated refinery apparatus wherein various streams are separated and fed to both a hydrocracking unit and a thermal cracking unit. Derwent WPI Accession No. 88-053890/08 for Japanese patent 60235890 discloses thermal cracking of hydrocarbons in a two stage system. Derwent WPI Accession No. 86-011144/02 for Japanese patent 63010693 discloses feeding by-product light oil containing olefins from a catalytic cracking unit to a thermal cracking furnace with prime olefins recovered in high purity.

Heretofore the art has not recognized that cracking an olefin mixture over suitable catalysts followed by thermal cracking can result in significant increases in production of prime olefins without prior separation of components or removal of $C_4+$ materials from the feed stream.

SUMMARY OF THE INVENTION

The present invention provides a process for improving the conversion of a hydrocarbon feedstock to light olefins comprising contacting the hydrocarbon feedstock with a light olefin producing cracking catalyst, preferably comprising a zeolite, in a catalyst contact zone followed by a catalyst-free thermal cracking step. The invention also allows one to alter the ratio of ethylene to propylene formed in the acid step.

DETAILED DESCRIPTION OF THE INVENTION

Definitions

"Light naphtha" means a hydrocarbon fraction that is predominantly $C_5$ to $C_7$ hydrocarbons.

"Virgin naphtha" means a hydrocarbon fraction obtained from crude oil or natural gas without additional conversion processing.

"Cat naphtha" means a refinery distillate fraction obtained by catalytic cracking of a heavier hydrocarbon fraction.

"BTX" means a mixture containing benzene, toluene, and xylenes.

"Light olefins" or "prime olefins" means ethylene, propylene or mixtures thereof.

"Improved conversion" means producing an increase in production that is a greater light olefin yield within the precision of the measurement system over cracking the same feedstock under the same conditions with the same catalyst without a subsequent thermal cracking step.

"Hydrocarbon feedstock" means a stream comprising one or more hydrocarbons to be broken into fragments by thermal, chemical or catalytic action, the fragments forming light olefins.

REACTION CONDITIONS AND CATALYSTS

Substantial amounts of ethylene and propylene are produced by cracking refinery or chemical feedstocks such as light cat naphtha (LCN) or light virgin naphtha (LVN) over catalysts; particularly zeolite containing catalysts such as those which contain ZSM-5. The present invention provides a method for enhancing ethylene and propylene yields which comprises contacting a hydrocarbon feedstock with an acidic zeolite catalyst followed by thermal cracking. Preferably the feed stream is LCN or LVN, but any catalyst crackable hydrocarbon stream may be used.

Any cracking catalyst operable to selectively produce prime olefins may be used in combination with a thermal cracking step. Suitable zeolites for use as the cracking catalyst are typically the acid form of any of the naturally-occurring or synthetic crystalline zeolites, especially those having a silica to alumina molar ratio within the range of about 2.0:1 to 2000:1. By employing the simple bench test described below, one skilled in the art can determine quickly whether a catalyst displays improved conversion by staging catalytic with thermal conversion.

Examples of zeolites useful in the claimed process include gallium silicate, zeolite beta, zeolite rho, ZK5, titanosilicate, ferrosilicate; borosilicate zeolites; zeolites designated by the Linde Division of Union Carbide by the letters of X, Y, A, L (these zeolites are described in U.S. Pat. Nos. 2,882,244; 3,130,007; 3,882,243; and 3,216,789, respectively); naturally occurring crystalline zeolites such as faujasite, chabazite, erionite, mazzite, mordenite, offretite, gmelinite, analcite, etc., and ZSM-5, as described in U.S. Pat. No. 3,702,886.

Particularly suitable catalysts are found among the medium and small pore zeolites. Such medium pore zeolites are considered to have a Constraint Index from about 1 to about 12. The method by which Constraint Index is determined is described fully in U.S. Pat. No. 4,016,218. Zeolites which conform to the specified values of Constraint Index for medium pore zeolites include ZSM-5, ZSM-11, ZSM-5/ZSM-11 intermediate, ZSM-12, ZSM-21, ZSM-22, ZSM-23, ZSM-35, ZSM-38, ZSM48, ZSM-50, MCM-22 and zeolite beta which are described, for example, in U.S. Pat. Nos. 3,702,886 and Re. No. 29,949, 3,709,979, 3,832,449, 4,046,859, 4,556,447, 4,076,842, 4,016,245, 4,229,424, 4,397,827, 4,954,325, 3,308,069, Re. 28,341 and EP 127, 399 to which reference is made for details of these catalysts. These zeolites may be produced with differing silica to alumina molar ratios ranging from 12:1 upwards. They have been, in fact, produced from reaction mixtures from which alumina is intentionally excluded, so as to produce materials having extremely high silica to alumina ratios which, in theory at least, may extend up to infinity. Preferred medium pore zeolites include ZSM-5, ZSM-11, ZSM-12, ZSM-35 and MCM-22. Particularly preferred is ZSM-5. Small pore zeolites, include such crystalline aluminosilicate zeolites as erionite, chabazite, ferrierite, heulandite, phillipsite, and such synthetic counterparts thereof as zeolites A and ZK5, as described in U.S. Pat. Nos. 2,882,243 and 3,247,195, respectively.

Preferably zeolites having a silica to alumina ratio within the range of about 2.0:1 to 2000:1 more preferably, the zeolite catalyst is selected from the group consisting of faujasite, chabazite, erionite, mordenite, offretite, gmelinite, analcite, phillipsite, ZSM-5, ZSM-11, ZSM-5/ZSM-11 intermediate, ZSM-12, ZSM-21, ZSM-22, ZSM-23, ZSM-35, ZSM-38, ZSM48, ZSM-50, MCM-22, gallium silicate, zeolite beta, zeolite rho, ZK5, titanosilicate, ferrosilicate; borosilicate, and zeolites designated by the Linde Division of Union Carbide by the letters of X, Y, and A. An especially favored zeolite is ZSM-5. Preparation of suitable zeolite containing catalysts may be carried out as described in the preceding references or purchased from commercial suppliers well known to those skilled in the art.

The catalytic cracking procedure can be carried out with any conventional equipment, which can be a fixed bed, moving bed, a fluidized bed, such as a riser or dense fluid bed system, or a stationary fluid bed system, and with typical refinery and chemical hydrocarbon feed streams. Preferably the catalyst is contacted at a temperature within the range of 500° C. to 750° C.; more preferably in the range of 550° C. to 725° C.; most preferably in the range of 650° C. to 720° C. Preferably the thermal step is carried out within the range of 650° C. to 900° C.; more preferably in the range of 680° C. to 800° C.; most preferably in the range of 700° C. to 760° C. The process is preferably carried out at a weight hourly space velocity (WHSV) in the range of about 0.1 $Hr^{-1}$ WHSV to about 100 $Hr^{-1}$ WHSV, more preferably in the range of about 1 $Hr^{-1}$ WHSV to about 50 $Hr^{-1}$ WHSV, and most preferably in the range of about 10 $Hr^{-1}$ WHSV to about 40 $Hr^{-1}$ WHSV. In the thermal cracking step the residence time is maintained in the range of 0.1 to 20 seconds, preferably 1 to 10 seconds, and most preferably for 6 to 9 seconds.

Examples of hydrocarbon streams which may be used to obtain high yields of light olefins include ethane, propane, butane, Fischer-Tropsch liquids, butenes, butadiene, steam cracked naphtha, and coker naphtha. A preferred feedstock is light cat naphtha (LCN) or light virgin naphtha (LVN).

The thermal cracking step may be conducted in the same vessel as the catalytic cracking by sizing the free board space volume above the catalyst bed appropriately to give the desired vapor residence time, if the thermal cracking step is to be carried out at the same or lower temperature as the catalytic cracking. Should it be necessary to carry out the thermal conversion step at a higher temperature than the catalytic cracking step, electrical firing or steam heat exchange can be used to elevate the reaction temperature.

An alternative embodiment to a reaction within a single vessel is a plurality of reactors in series with the down stream operated to provide the desired thermal cracking conditions independent of the catalytic cracking conditions.

EXAMPLE 1

A series of runs in a small bench reactor was conducted on hexane model compounds. A first run was conducted at 710° C., 36 $Hr^{-1}$ WHSV over a fixed bed of 0.6 g ZCAT40, a ZSM-5 zeolite catalyst commercially available from Intercat. Inc., of Sea Girt, N.J. Prior to the cracking tests, ZCAT40 was steamed with 100% steam at 704° C. and 1 atmosphere for 16 hours for the purpose of aging the catalyst. The yields of key products from this run are given in the first column of Table 1. A blend of model compounds was created corresponding to the effluent from the catalytic cracking step consisting of hydrogen, methane, ethylene, ethane, propylene, propane, butylenes, butane, hexane and benzene. This model compound blend was then subjected to thermal cracking at 710° C. for 6.1 and 9.2 seconds. A third run treated the same model compound blend at 740° C. for 5.9 seconds. In test runs, steam to hydrocarbon weight ratio was 0.33. The effluent stream was analyzed by on-line gas chromatography. A column having a length of 60 m packed with fused silica was used for the analysis. The GC used was a dual FID Hewlett-Packard Model 5880.

The results are tabulated below:

TABLE 1

CATALYTIC + THERMALCRACKING AT 710° C.

| Added Thermal Cracking Residence Time, seconds | None | 6.1 | 9.2 |
|---|---|---|---|
| Conversion, Wt % | 84.4 | 89.6 | 90.8 |
| Key Product Yields, Wt % | | | |
| Ethylene | 27.7 | 30.7 | 31.4 |
| Propylene | 23.9 | 24.2 | 23.3 |
| Aromatics | 2.7 | 3.0 | 3.9 |
| Light saturates | 21.3 | 25.7 | 26.7 |

As shown in Table 1, when hexane model compound was cracked over ZCAT40 at 710° C. and 36 hr$^{-1}$ WHSV, conversion was 84.4 wt %, while ethylene and propylene yields were 27.7 wt % and 23.9 wt %, respectively. When the model compound blend representing the effluent from this acid cracking step was subjected to thermal cracking at 710° C. for 6.1 up to 9.2 seconds, ethylene yield increased to 30.7–31.4 wt % from 27.7 wt %, while propylene yield remained nearly constant at 23–24 wt %.

TABLE 2

CATALYTIC + THERMALCRACKING AT 740° C.

| Added Thermal Cracking Residence Time, seconds | None | 6.1 |
|---|---|---|
| Conversion, Wt % | 84.4 | 93.3 |
| Key Product Yields, Wt % | | |
| Ethylene | 27.7 | 33.7 |
| Propylene | 23.9 | 23.5 |
| Aromatics | 2.7 | 3.8 |
| Light saturates | 21.3 | 28.3 |

In Table 2, the model compound blend representing the effluent from acid cracking of hexane model compound at 710° C. and 36 hr$^{-1}$ WHSV was subject to thermal cracking at 740° C. for 6.1 seconds. Ethylene yield increased to 33.7 wt % from 27.7 wt %. Once again, propylene yield was very stable, between 23–24 wt %.

TABLE 3

Summary

| Case | Catalytic + Thermal | Catalytic Only | Thermal Only |
|---|---|---|---|
| Cat. cracking Temperature | 710.0 | 710.0 | none |
| WHSV based on Catalyst Hr.$^{-1}$ | 36.0 | 24.0 | none |

TABLE 3-continued

Summary

| Case | Catalytic + Thermal | Catalytic Only | Thermal Only |
|---|---|---|---|
| Thermal Cracking Temperature, ° C. | 740.0 | none | 800.0 |
| TC Vapor Residence Time, Sec. | 6.1 | none | 0.9 |
| Conversion Wt. % | 93.3 | 92.8 | 91.4 |
| Key Results Wt. % | | | |
| Ethylene | 33.7 | 30.6 | 30.8 |
| Propylene | 23.5 | 25.3 | 18.0 |
| Aromatics | 3.8 | 5.0 | 7.8 |
| Light Saturates | 28.3 | 25.9 | 26.6 |

Table 3 offers a comparison of catalytic plus thermal cracking with straight catalytic cracking and straight thermal cracking at 91–93 wt % conversion. As can be seen from the table, catalytic plus thermal cracking resulted in 3 wt % more ethylene than straight catalytic cracking. Catalytic plus thermal cracking also compared favorably with straight thermal conversion. At 91–93 wt % conversion, propylene yield is 5–6 wt % higher with catalytic plus thermal cracking as compared to straight thermal cracking.

We claim:

1. A process for improving conversion of a hydrocarbon feedstock to light olefins comprising:

first contacting the hydrocarbon feedstock with a light olefin-producing cracking catalyst at a temperature in the range of 500° C. to 750° and the feedstock flows at a weight hourly space velocity in the range of 0.1 Hr-1 to 100 Hr-1; and subsequently thermally converting the effluent stream without separation of reaction products at a thermal conversion temperature in the range of 650° C. to 900° C. with a residence time of 0.1 to 20 sec. to produce additional ethylene.

2. The process of claim 1 wherein the cracking catalyst comprises a zeolite having a silica to alumina ratio within the range of about 2.0:1 to 2000:1.

3. The process of claim 2 wherein the zeolite is selected from the group consisting of ferrierite, heulandite, mazzite, phillipsite, faujasite, chabazite, erionite, mordenite, offretite, gmelinite, analcite, ZSM-5, ZSM-11, ZSM-5/ZSM-11 intermediate, ZSM-12, ZSM-21, ZSM-22, ZSM-23, ZSM-35, ZSM-38, ZSM48, ZSM-50, MCM-22 and zeolite beta, gallium silicate zeolite, zeolite rho, ZK5, titanosilicate, ferrosilicate; borosilicate zeolites; and zeolites designated by the Linde Division of Union Carbide by the letters of X, Y, and A.

4. The process of claim 3 wherein the zeolite catalyst comprises ZSM-5.

5. The process of claim 1 wherein the hydrocarbon feedstock is selected from the group consisting of Fischer-Tropsch liquid, ethane, propane, butane, butene, butadiene, steam cracked naphtha, coker naphtha, light cat naphtha and light virgin naphtha, kerosene, and gasoil.

6. The process of claim 1 wherein the catalyst is contacted at a temperature within the range of 550° C. to 725° C.

7. The process of claim 1 wherein the feedstock flow is in the range of 1 Hr-1 to 50 Hr-1.

8. The process of claim 1 wherein the catalyst is contacted at a temperature within the range in the range of 650° C. to 720° C.

9. The process of claim 1 wherein the feedstock flow is in the range of 10 Hr-1 to 40 Hr-1.

10. In a process for producing ethylene and propylene in a catalytic cracking process wherein a hydrocarbon feedstock is contacted with an acidic zeolite cracking catalyst, the improvement which comprises providing a catalyst cracking zone and providing a thermal cracking zone downstream from the catalyst cracking zone.

11. The process of claim 10 wherein the cracking catalyst comprises a zeolite.

12. The process of claim 11 wherein the zeolite catalyst is selected from the group consisting of ferrierite, mazzite, phillipsite, heulandite, faujasite, chabazite, erionite, mordenite, offretite, gmelinite, analcite, ZSM-5, ZSM-11, ZSM-5/ZSM-11 intermediate, ZSM-12, ZSM-21, ZSM-22, ZSM-23, ZSM-35, ZSM-38, ZSM48, ZSM-50, MCM-22 and gallium silicate zeolite, zeolite beta, zeolite rho, ZK5, titanosilicate, ferrosilicate; borosilicate zeolites; zeolites designated by the Linde Division of Union Carbide by the letters of X, Y, and A.

13. The process of claim 10 wherein the catalyst is contacted at a temperature within the range of 500° C. to 750° C. and the feedstock flows at a weight hourly space velocity in the range of 0.1 $Hr^{-1}$ to 100 $Hr^{-1}$ and the thermal cracking step is carried out at a temperature within the range of 650° C. to 900° C. with a residence time of 0.1 to 20 seconds.

14. The process of claim 13 wherein the zeolite comprises ZSM-5.

15. The process of claim 13 wherein the feedstock is selected from the group consisting of Fischer-Tropsch liquid, ethane, propane, butane, butene, butadiene, steam cracked naphtha, coker naphtha, light cat naphtha and light virgin naphtha, kerosene, and gasoil.

16. The process of claim 15 wherein the catalyst is contacted at a first catalyst contact zone temperature within the range of 650° C. to 720° C. and the feedstock flows at a weight hourly space velocity in the range of 10 $Hr^{-1}$ to 40 $Hr^{-1}$ and the thermal cracking step is carried out at a temperature within the range of 700° C. to 760° C. with a residence time of 6 to 9 seconds.

17. The process of claim 1 wherein the thermal cracking step is carried out at a temperature within the range of 680° C. to 800° C.

18. The process of claim 13 wherein the thermal cracking step is carried out at a temperature within the range of 680° C. to 800° C.

19. The process of claim 1 wherein the thermal cracking step is carried out with a residence time of 1 to 10 seconds.

20. The process of claim 13 wherein the thermal cracking step is carried out with a residence time of 1 to 10 seconds.

* * * * *